United States Patent
Gharda

(10) Patent No.: US 9,533,998 B2
(45) Date of Patent: Jan. 3, 2017

(54) CARBAZOLE DIOXAZINE PIGMENTS

(71) Applicant: Keki Hormusji Gharda, Maharashtra (IN)

(72) Inventor: Keki Hormusji Gharda, Maharashtra (IN)

( * ) Notice: Subject to any disclaimer, the term of this patent is extended or adjusted under 35 U.S.C. 154(b) by 0 days.

(21) Appl. No.: 14/786,606

(22) PCT Filed: Apr. 25, 2014

(86) PCT No.: PCT/IN2014/000264
§ 371 (c)(1),
(2) Date: Oct. 23, 2015

(87) PCT Pub. No.: WO2014/181348
PCT Pub. Date: Nov. 13, 2014

(65) Prior Publication Data
US 2016/0096849 A1    Apr. 7, 2016

(30) Foreign Application Priority Data

Apr. 26, 2013  (IN) .......................... 1531/MUM/2013

(51) Int. Cl.
*C07D 498/22*  (2006.01)
*C08K 5/3417*  (2006.01)
*C08K 5/3437*  (2006.01)
*C07D 209/62*  (2006.01)

(52) U.S. Cl.
CPC ........... *C07D 498/22* (2013.01); *C07D 209/62* (2013.01); *C08K 5/3417* (2013.01); *C08K 5/3437* (2013.01)

(58) Field of Classification Search
CPC .... C07D 498/22; C08K 5/3417; C08K 5/3437
USPC .......................................................... 544/74
See application file for complete search history.

(56) References Cited

U.S. PATENT DOCUMENTS

| | | | |
|---|---|---|---|
| 4,345,074 A | 8/1982 | Hufnagel et al. | |
| 4,751,300 A | 6/1988 | Fujita et al. | |
| 6,476,222 B2 | 11/2002 | Smith et al. | |

FOREIGN PATENT DOCUMENTS

| | | |
|---|---|---|
| GB | 599252 | 3/1948 |
| WO | 2012/001708 A1 | 1/2012 |

OTHER PUBLICATIONS

International Search Report of PCT/IN2014/000264 mailed Sep. 30, 2014.

*Primary Examiner* — Kahsay Habte
(74) *Attorney, Agent, or Firm* — Muncy, Geissler, Olds & Lowe, P.C.

(57) ABSTRACT

The present disclosure relates to a benzoyl substituted carbazole-dioxazine pigment and its preparation. The process involves benzoylation of 3-nitro-N-ethylcarbazole in monochlorobenzene using benzoylchloride and ferric chloride to yield 3-nitro-6-benzoyl-N-ethyl carbazole, which on catalytic hydrogenation and subsequent condensation with chloranil and cyclization yields benzoyl substituted carbazole-dioxazine pigment.

11 Claims, No Drawings

CARBAZOLE DIOXAZINE PIGMENTS

This application is a national stage of International Application No.: PCT/IN2014/000264, which was filed on Apr. 25, 2014, and which claims priority to IN 1531/MUM/2013 which was filed on Apr. 26, 2013, and which are both herein incorporated by reference.

FIELD OF DISCLOSURE

The present disclosure relates to a dioxazine pigment and a process for synthesizing the same.

Particularly, the present disclosure relates to a carbazole-dioxazine pigment and a process for synthesizing the same.

BACKGROUND

Dioxazine compounds are used in the synthesis of valuable dyes and pigments. These compounds are typically prepared by a five-stage synthesis process which involves N-alkylation of carbazole, followed by nitration, reduction, condensation and ring closure.

Pigment violet 23 is one of pigments belonging to Dioxazine class. In the recent past, it has gained significant importance due to its outstanding properties as a colorant.

Structure:

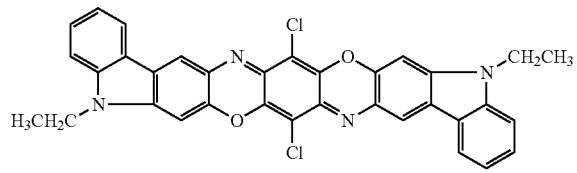

Molecular Formula: $C_{34}H_{22}Cl_2N_4O_2$
Molecular Weight: 589.47
CAS Registry Number: 6358-30-1

Pigment violet-23 (carbazole violet) belongs to dioxazine class, with color ranging from bluish-red to violet shade and is used in various applications such as paint, plastic, inks, coatings and the like.

Pigment violet 23 is obtained by cyclization of 2,5-di-(9-ethylcarbazol-3-ylamino)-3,6-dichloro-1,4-benzoquinone which is synthesized by reacting chloranil (tetrachloro-p-benzoquinone) with 3-amino-9-ethylcarbazole.

U.S. Pat. No. 4,345,074 discloses synthesis of Pigment violet 23 by condensing and cyclizing 3-amino-9-ethylcarbazole with excess tetrachlorobenzoquinone in an organic solvent in the presence of acid acceptors. The process particularly focuses on carrying out the condensation reaction in the presence of 0.1 to 4% of water in order to avoid fluctuation in the yield.

U.S. Pat. No. 6,476,222 discloses a process for improving the heat stability of Pigment Violet 23 by conditioning crude Pigment Violet 23. The conditioning is carried out by grinding the crude pigment in the presence of a grinding agent and an organic solvent.

WO2012001708 discloses a process for preparing dioxazine pigments such as Pigment Violet 23, which avoids the formation of by-products. The process involves cyclization of 2,5-di-(9-ethylcarbazol-3-ylamino)-3,6-dichloro-1,4-benzoquinone in the presence of air (enriched with 19-20% of oxygen).

The known prior art processes provides synthesis of carbazole-dioxazine pigment such as Pigment Violet 23. However, there is a need for synthesizing and exploring hitherto unknown variants of carbazole-dioxazine pigment in order to exploit the inherent colour strength of dioxazine chromophore with improvement in the pigmentory properties like viscosity, transparency, gloss, heat stability, color strength and durability properties relative to Pigment Violet 23.

OBJECT

Some of the objects of the present disclosure, which at least one embodiment herein satisfies, are as follows:

It is an object of the present disclosure to provide a new variant of carbazole-dioxazine pigment having improved pigmentory properties relative to Pigment Violet 23.

Other objects and advantages of the present disclosure will be more apparent from the following description, which are not intended to limit the scope of the present disclosure.

SUMMARY

The present disclosure provides a process for the synthesis of a carbazole-dioxazine pigment of formula I;

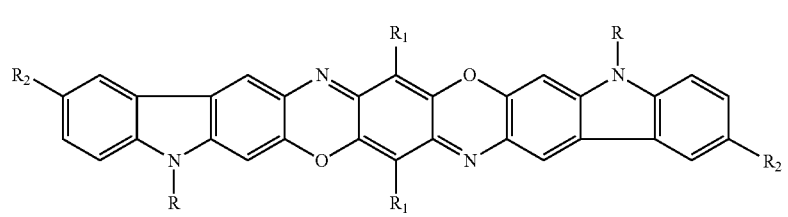

Formula I wherein,

R is $C_1$-$C_8$ alkyl group, preferably R is an ethyl group, $R_1$ is a chloro group, and $R_2$ is a benzoyl group, said process comprising the following steps:

a) reacting 3-nitro-N-ethylcarbazole with benzoylchloride in the presence of monochlorobenzene and ferric chloride to obtain 3-nitro-6-benzoyl-N-ethyl carbazole;

b) hydrogenating said 3-nitro-6-benzoyl-N-ethyl carbazole in the presence of a catalyst and a promoter in a solvent to obtain 6-benzoyl-3-amino-N-ethyl carbazole;

c) condensing 6-benzoyl-3-amino-N-ethyl carbazole with chloranil in the presence of a solvent and sodium acetate to obtain an intermediate of formula II; and Formula II

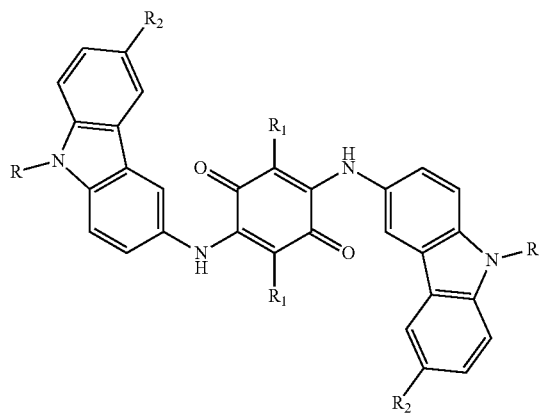

wherein, R is $C_1$-$C_8$ alkyl group, preferably R is an ethyl group,
$R_1$ is a chloro group, and
$R_2$ is a benzoyl group, d) cyclizing the intermediate using a cyclizing agent to obtain carbazole-dioxazine pigment of formula I.

Typically, the catalyst is Raney nickel.

Typically, the cyclizing agent is benzene sulfonyl chloride.

Typically, the solvent is at least one selected from the group consisting of ortho-dichlorobenzene, monochlorobenzene and a combination thereof.

Typically, the step (a) is carried out at a temperature ranging from 90 to 120° C.

Typically, the step (b) is carried out at a temperature ranging from 120 to 140° C. and at a pressure ranging from 10 to 16 kg/cm².

Typically, the step (c) is carried out at a temperature ranging from 45 to 70° C.

Typically, the step (d) is carried out at a temperature ranging from 140 to 180° C.

Typically, the promoter is sodium phosphate dibasic.

In accordance with another aspect of the present disclosure there is provided a carbazole-dioxazine pigment of formula I;

Formula I

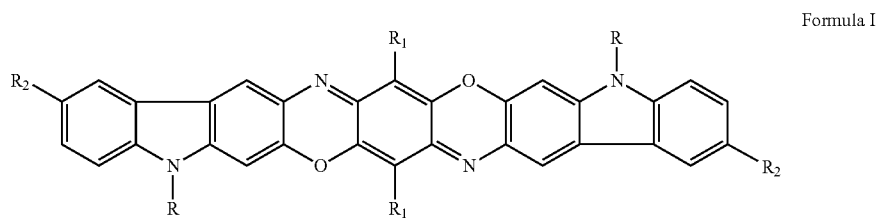

wherein,
R is $C_1$-$C_8$ alkyl group, preferably R is an ethyl group,
$R_1$ is a chloro group; and
$R_2$ is a benzoyl group;

Typically, the pigment is characterized by surface area of from 50 m²/g to 80 m²/g;

DESCRIPTION

The present disclosure provides a variant of known carbazole-dioxazine pigment, namely Pigment Violet-23. Particularly, the present disclosure provides a novel benzoyl substituted variant of Pigment Violet-23 which is represented by formula I.

Formula I

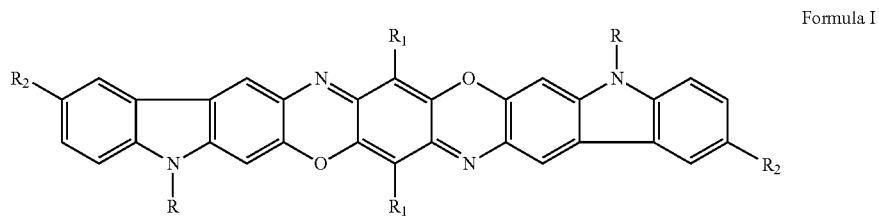

wherein,

R is $C_1$-$C_8$ alkyl group, preferably R is an ethyl group,
$R_1$ is a chloro group, and $R_2$ is a benzoyl group.

In accordance with the present disclosure benzoyl substituted Pigment Violet 23 also herein referred as PV-23 homologue-I, is prepared using 3-nitro-6-benzoyl-N-ethyl carbazole. 3-nitro-N-ethylcarbazole in monochlorobenzene is benzoylated using benzoylchloride and ferric chloride to yield 3-nitro-6-benzoyl-N-ethyl carbazole, which on catalytic hydrogenation in the presence of a promoter in a chlorinated benzene solvent and subsequent condensation with chloranil and cyclisation yields benzoyl substituted Pigment Violet 23 homologue-I.

In accordance with exemplary embodiment the process involves the following steps:

In the first step, 3-nitro-N-ethylcarbazole is reacted with benzoylchloride in the presence of monochlorobenzene and ferric chloride to obtain 3-nitro-6-benzoyl-N-ethyl carbazole.

This step of benzoylation is carried out at a temperature ranging from 90 to 120° C.

In the next step, 3-nitro-6-benzoyl-N-ethyl carbazole is hydrogenated in the presence of a catalyst and a promoter in a solvent to obtain 6-benzoyl-3-amino-N-ethyl carbazole. The catalyst employed includes but is not limited to Raney nickel and the solvent is selected from the group consisting of ortho-dichlorobenzene, monochlorobenzene and a combination thereof. The step of hydrogenation is carried out at a temperature ranging from 120 to 140° C. and at a pressure ranging from 10 to 16 kg/cm². The promoter employed in the hydrogenation reaction is sodium phosphate dibasic.

The obtained 6-benzoyl-3-amino-N-ethyl carbazole is condensed with chloranil in the presence of a solvent and sodium acetate to obtain an intermediate of formula II.

Formula II

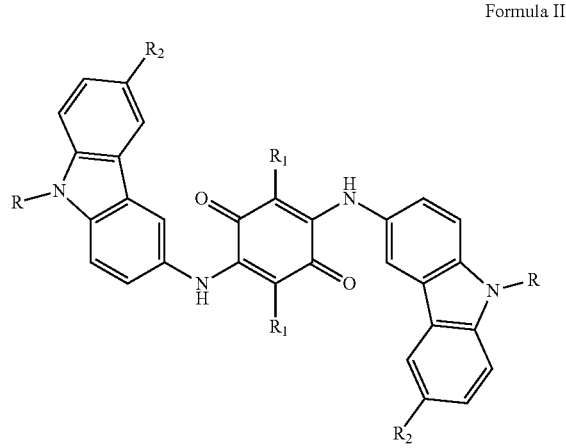

The intermediate of formula II is then cyclized using a cyclizing agent to obtain carbazole-dioxazine pigment of formula I. The cyclizing agent includes but is not limited to benzene sulfonyl chloride. The condensation step is carried out at a temperature ranging from 45 to 70° C., whereas the cyclization is carried out at a temperature ranging from 140 to 180° C.

The obtained pigment is characterized by surface area of from 50 m²/g to 80 m²/g. The synthesized pigment is characterized by FTIR spectra, elemental analysis and GC-MS and is found to be in agreement with the molecular formula and molecular weight respectively. The physical properties, fastness properties, and solvent resistance properties of the homologue-1 pigment are also studied and found to be satisfactory. The prepared homologue-1 showed heat stability (upto 280° C.).

The chemical resistance properties (in 5% hydrochloric & 5% sodium hydroxide) are also found to be satisfactory.

Further, solvent fastness (w.r.t. water, xylene, methyethylketone, N-Butanol, PEG, DOP, butyl acetate and mineral turpentine and the like) and the migration fastness property is found to be good to excellent.

The visible absorption spectra of the present pigment (in dimethylformamide) show λmax at 601 nm, whereas PV-23 shows λmax at 570 nm.

The study of colour values of the pigment draw-downs is also carried out. The CIE attributes of lightness (L*), chroma (C*), hue (h*) and colour (a*, b*) are determined by colorimetric assessment of pigment drawdown.

The disclosure is further illustrated with the help of following working examples which should not be construed to limit the disclosure in any way.

Example 1

Step: I: Benzoylation of Nitroethylcarbazole

Nitroethylcarbazole (NEC) having purity of 98.8% was crystallized from monochlorobenzene solvent to yield 99.5% pure NEC. 100 gms of purified NEC (0.417 moles) was charged into a reactor vessel containing monochlorobenzene (300 ml) and the mixture was stirred at a temperature of 32° C. for a period of 15 minutes. The temperature of the mixture was then raised to 75° C. and 0.5 gm of ferric chloride (0.031 moles) was added to the mixture followed by drop-wise addition of 77 gm benzoyl chloride (0.548 moles) at a temperature of 100° C. over a period of 5-6 hours. During the benzoylchloride addition, hydrochloric acid was generated. Reaction was continued at a temperature of 115° C. over a period 20 hours till the evolution of the HCl gas ceased. The reacted mixture was then cooled to 90° C., refluxed for 1 hour in the presence of 1N HCl and then further cooled to yield greenish colour benzoylated nitroethylcarbazole (Bz-NEC). Crude benzoylated NEC (Bz-NEC) was then purified by crystallization using monochlorobenzene to yield pure Bz-NEC. Yield of pure Bz-NEC was 60%. The compound Bz-NEC was characterized by FTIR and NMR spectroscopy. The spectroscopic analysis confirms the compound 6-Benzoyl-3-nitro-9N-ethylcarbazole. HPLC and melting point test were also performed to confirm that compound is 6-Benzoyl-3-nitro-9N-ethylcarbazole.

Characteristic properties of 6-Benzoyl-3-Nitro-9N-ethyl-carbazole:

Melting point: 217-219° C.

FTIR: peak at 1593 cm-1 indicates the presence of carbonyl group.

NMR: peaks at δ 7-9 cm$^{-1}$ corresponds to aromatic protons, the quadrate at δ 4.4-4.5 cm$^{-1}$ corresponds to 2H of $CH_2$ and the triplet at δ 1.5-1.6 cm$^{-1}$ corresponds to 3H of $CH_3$.

Response factor for NEC to Benzoyl on HPLC was found as follows:

| Actual Ratio | | Observed Ratio | |
|---|---|---|---|
| NEC | Benzyolated NEC | NEC | Benzyolated NEC |
| 75 | 25 | 52 | 48 |
| 50 | 50 | 26 | 74 |
| 25 | 75 | 11 | 89 |
| 2 | 98 | 0.9 | 99.1 |

Step II: Hydrogenation of Benzoylated Nitroethylcarbazole (Bz-NEC)

90 gm of Bz-NEC (0.26 moles) as obtained in the first step and ortho-dichlorbenzene (1000 ml) were charged in a 2-lit autoclave, to this mixture, raney nickel catalyst (16 gm-wet) and sodium phosphate dibasic (1.04.gm) was added and the mixture was then hydrogenated at a temperature of 130° C. and at a hydrogen pressure of 10-16 kg for a period of 9-15 hours. The reaction was monitored by TLC, till it showed absence of the starting compound. The product yield was 92%. The product was characterized by NMR and FTIR, which confirmed the product to be 6-Benzoyl-3-amino-9-Nethyl carbazole. Characteristic properties of 6-Benzoyl-3-Amino-9N-ethylcarbazole (Bz-ACE): NMR: The peaks at δ 7-9 $cm^{-1}$ corresponds to aromatic protons, the singlet at δ 2.23 $cm^{-1}$ corresponds to 2H of $NH_2$, the quadrate at δ 3.0 $cm^{-1}$ corresponds to 2H of $CH_2$, the triplet at δ 1.89 $cm^{-1}$ corresponds to 3H of $CH_3$. From the NMR it is clear that the carbonyl group is not hydrogenated during the reaction.

FTIR spectra show a peak at 3431 $cm^{-1}$ which indicates the presence of primary amino group and a peak at 1597 $cm^{-1}$ which indicates the presence of carbonyl group.

Step III: Condensation and Cyclization 76 gms Bz-ACE (0.242 moles) and ortho-dichlorobenzene (900 ml) were charged in a reactor vessel to obtain a mixture. To this, sodium acetate 40 gms (0.30 moles) and 45 gm chloranil (0.182 moles) were added at a temperature of 45° C., the mixture was then stirred for a period of 10 minutes and heated further to 65° C. for a period of 5 hours. The reaction was monitored by TLC. After the completion of reaction, acetic acid formed was removed along with ortho-dichlorobenzene by distillation at 90° C. and 640 mmHg vacuum, over a period of 3-5 hours. After the complete removal of acetic acid, the reacted mixture was cyclized by adding 28.8 gms of benzene sulfonyl chloride (0.16 moles). The addition was carried out drop-wise at 140° C. over a period of 1 hr. Temperature was slowly raised to 175° C. and maintained for a period of 6 hours. The product mixture so formed was cooled to 90° C. and the product was isolated by filtration. The filtered product was washed with hot ortho-dichlorobenzene, with methanol and finally with water and then dried in oven at 80° C. to yield 75% of crude carbazole-dioxazine pigment.

Step IV: Finishing

The dried crude pigment was salt kneaded in a kneader in the presence of diethyl glycol (DEG) in the ratio (1 part pigment:10 part salt:4 parts DEG) for a period of 10 hrs at 50° C. The kneaded product was heated to 80° C. in water and further treated with 5% concentrated HCL for a period of 1-2 hrs at 70° C. The treated product was filtered, washed with water till it was salt free and had neutral pH, with conductivity less than 500 micron. The wet cake was further refluxed with isobutyl alcohol in the presence of caustic lye at a temperature of 90° C. for a period of 3-4 hours, the isobutyl alcohol water mixture was removed by distillation and the residue was washed with water till pH was adjusted to 7 and then further washed with distilled water till the conductivity was less than 500 micron. The washed residue was than dried at 80-90° C. and then pulverized.

The product was characterized by elemental analysis, GCMS, IR spectra which was in agreement with the structure. The XRD Peak profile was found to be different than that of PV 23.

Testing of the pigment as obtained in step IV:

The pigment PV-23 homologue-1 showed high blue colour than existing PV-23 in aqueous, air dried paint and also in muller test.

Physical Characterization of the pigment PV-23 homologue-1:

XRD analysis: Peak profile is different from that of PV 23.
Surface area: 69.91 $m^2/gm$
Coloristic Results:
Visual—Reddish blue color with good transparency and tinting strength.
Instrumental:
Lab Values—Plastic

| | Illum* | L* | a* | b* | C* | h° |
|---|---|---|---|---|---|---|
| PV 23 | D65 | 34.22 | 10.55 | −49.92 | 51.03 | 281.94 |
| Homologue # | CWF_2 | 28.66 | 11.58 | −59.72 | 60.84 | 280.98 |
| 9A PVC FT | A | 29.10 | −1.86 | −58.05 | 58.08 | 268.16 |
| PV 23 | D65 | 47.45 | 3.15 | −36.76 | 36.90 | 274.90 |
| Homologue # | CWF_2 | 43.23 | 4.34 | −44.35 | 44.57 | 275.59 |
| 9A PVC RN | A | 44.08 | −3.34 | −41.80 | 41.94 | 265.44 |

Lab Values—Paint

| | Illum* | L* | a* | b* | C* | h° |
|---|---|---|---|---|---|---|
| PV 23 | D65 | 20.424 | −0.083 | −0.001 | 0.083 | 180.7 |
| Homologue # 9A SPFS | CWF_2 | 20.423 | −0.289 | 0.157 | 0.329 | 151.545 |
| | A | 20.44 | 0.21 | −0.16 | 0.26 | 322.01 |
| PV 23 | D65 | 48.722 | 0.663 | −31.244 | 31.251 | 271.215 |
| Homologue # 9A SPRN | CWF_2 | 45.66 | 1.675 | −36.918 | 36.956 | 272.598 |
| | A | 45.79 | −6.22 | −35.55 | 36.09 | 260.08 |

Illuminants*
D65—Day light, CWF_2—Fluorescent, A—Tungsten

Paint Application Properties:

| Properties | Result |
|---|---|
| 1. Chemical Resistance (1-5 gray scale) | |
| 1.1. Acid (2%) | 4 |
| 1.2. Alkali (2%) | 3 |
| 2. Resistance to solvents (1-5 gray scale) | |
| 2.1. Water | 5 |
| 2.2. Mineral Turpentine oil | 5 |
| 2.3. n-Butanol | 5 |
| 2.4. Butyl acetate | 4 |
| 2.5. Xylene | 4 |
| 2.6. MEK | 4 |
| 2.7. PEG | 5 |
| 2.8. DOP | 5 |

-continued

| Properties | Result |
| --- | --- |
| 3. Heat stability-Alkyd/Melamine paint-full shade @ 30 minutes baking | 130° C. |
| 4. Heat stability-Alkyd/Melamine paint-reduction @ 30 minutes baking | 180° C. |
| 5. Weather fastness (1-5 gray scale) | |
| 5.1. Alkyd/Melamine-FS | 1 |
| 5.2. Alkyd/Melamine-1/3SD | 2-3 |
| 5.3. Alkyd/Melamine-1/25SD | 2 |
| 6. Over coating fastness (1-5 gray scale) | 5 |

Plastic Application Properties:

| Properties | Result |
| --- | --- |
| 1. Chemical Resistance (1-5 Gray scale) | |
| 1.1. Acid (2%) | 4 |
| 1.2. Alkali (2%) | 3 |
| 2. Heat stability-HDPE reduction @ 5 minutes dwelling. | 280° C. (Violet patches seen on chips) |
| 3. Migration fastness-PVC (1-5 Gray scale) | 4 |

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results.

Any discussion of documents, acts, materials, devices, articles or the like that has been included in this specification is solely for the purpose of providing a context for the invention. It is not to be taken as an admission that any or all of these matters form part of the prior art base or were common general knowledge in the field relevant to the invention as it existed anywhere before the priority date of this application.

While considerable emphasis has been placed herein on the preferred embodiment, it will be appreciated that many embodiments can be made and that many changes can be made in the preferred embodiments without departing from the principles of the disclosure. These and other changes in the preferred embodiments of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:

1. A process for the synthesis of a carbazole-dioxazine pigment of Formula I;

Formula I

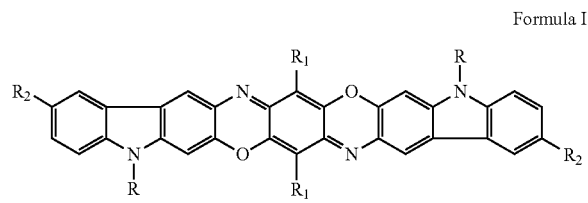

wherein,

R is $C_1$-$C_8$ alkyl group, $R_1$ is a chloro group, and $R_2$ is a benzoyl group, said process comprising the following steps:

a) reacting 3-nitro-N-ethyl carbazole with benzoylchloride in the presence of monochlorobenzene and ferric chloride to obtain 3-nitro-6-benzoyl-9N-ethyl carbazole;

b) hydrogenating said 3-nitro-6-benzoyl-9N-ethyl carbazole in a solvent in the presence of Raney nickel catalyst and sodium phosphate dibasic to obtain 6-benzoyl-3-amino-9N-ethyl carbazole;

c) condensing 6-benzoyl-3-amino-9N-ethyl carbazole with chloranil in the presence of a solvent and sodium acetate to obtain an intermediate of formula II; and Formula II

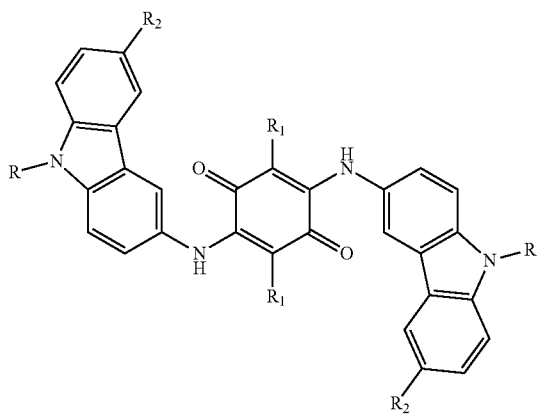

wherein,

R is $C_1$-$C_8$ alkyl group, $R_1$ is a chloro group, and $R_2$ is a benzoyl group, d) cyclizing the intermediate using a cyclizing agent to obtain carbazole-dioxazine pigment of formula I.

2. The process as claimed in claim 1, wherein the cyclizing agent is benzene sulfonyl chloride.

3. The process as claimed in claim 1, wherein the solvent is selected from the group consisting of ortho-dichlorobenzene, monochlorobenzene and a combination thereof.

4. The process as claimed in claim 1, wherein the step (a) is carried out at a temperature ranging from 90 to 120° C.

5. The process as claimed in claim 1, wherein the step (b) is carried out at a temperature ranging from 120 to 140° C. and at a pressure ranging from 10 to 16 kg/cm$^2$.

6. The process as claimed in claim 1, wherein the step (c) is carried out at a temperature ranging from 45 to 70° C.

7. The process as claimed in claim 1, wherein the step (d) is carried out at a temperature ranging from 140 to 180° C.

8. A carbazole-dioxazine pigment of formula I;

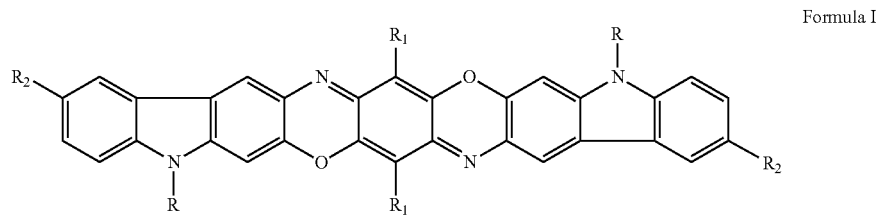

Formula I wherein,
R is $C_1$-$C_8$ alkyl group,
$R_1$ is a chloro group; and
$R_2$ is a benzoyl.

9. The carbazole-dioxazine pigment of formula I as claimed in claim 8, wherein said pigment is characterized by surface area of from 50 $m^2/g$ to 80 $m^2/g$.

10. The process as claimed in claim 1, wherein R is an ethyl group.

11. The carbazole-dioxazine pigment as claimed in claim 8, wherein R is an ethyl group.

* * * * *